United States Patent
Kang et al.

(10) Patent No.: US 10,119,918 B2
(45) Date of Patent: Nov. 6, 2018

(54) ADJUSTABLE COLORIMETRIC MOISTURE INDICATORS

(71) Applicant: 3M INNOVATIVE PROPERTIES COMPANY, St. Paul, MN (US)

(72) Inventors: Myungchan Kang, Woodbury, MN (US); Evan Koon Lun Yuuji Hajime, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 597 days.

(21) Appl. No.: 14/441,478

(22) PCT Filed: Nov. 14, 2013

(86) PCT No.: PCT/US2013/070061
§ 371 (c)(1),
(2) Date: May 7, 2015

(87) PCT Pub. No.: WO2014/078512
PCT Pub. Date: May 22, 2014

(65) Prior Publication Data
US 2015/0293028 A1    Oct. 15, 2015

Related U.S. Application Data (60) Provisional application No. 61/726,251, filed on Nov. 14, 2012.

(51) Int. Cl.
*G01N 21/00* (2006.01)
*G01N 21/81* (2006.01)
(Continued)

(52) U.S. Cl.
CPC .............. *G01N 21/81* (2013.01); *B01J 20/08* (2013.01); *B01J 20/103* (2013.01); *B01J 20/223* (2013.01);
(Continued)

(58) Field of Classification Search
CPC ...................................................... G01N 21/81
(Continued)

(56) References Cited

U.S. PATENT DOCUMENTS 2,580,737 A    1/1952   Davis
2,627,505 A    2/1953   Goodwin
(Continued)

FOREIGN PATENT DOCUMENTS

CN    1576801 A    2/2005
CN    101432617 A    5/2009
(Continued)

OTHER PUBLICATIONS

Yu. G. Slizhov and M. A. Gavrilenko Journal of Analytical Chemistry, vol. 56, No. 6, 2001, pp. 538-541 (Year: 2001).*

(Continued)

*Primary Examiner* — Christine T Mui
*Assistant Examiner* — Emily R. Berkeley
(74) *Attorney, Agent, or Firm* — Qiang Han (57) ABSTRACT

Compositions are provided comprising: 1) a solid metal oxide support having surface hydroxyl groups; 2) a silyl-containing compound bound to the solid metal oxide support through a silanol bond with the surface hydroxyl groups; and 3) a bis(glyoxime)-transition metal complex bound to the solid metal oxide support. These compositions can be used to make a colorimetric relative humidity-indicating sensor. A method of adjusting the colorimetric response of a moisture-indicating composition and a method of detecting moisture are also provided.

25 Claims, 4 Drawing Sheets

(51) Int. Cl.

| | | |
|---|---|---|
| *G01N 31/22* | (2006.01) | |
| *B01J 20/08* | (2006.01) | |
| *B01J 20/22* | (2006.01) | |
| *B01J 20/32* | (2006.01) | |
| *B01J 20/28* | (2006.01) | |
| *B01J 20/10* | (2006.01) | |
| *G01N 21/77* | (2006.01) | |

(52) U.S. Cl.
CPC ... *B01J 20/28016* (2013.01); *B01J 20/28057* (2013.01); *B01J 20/3204* (2013.01); *B01J 20/3236* (2013.01); *B01J 20/3248* (2013.01); *G01N 31/222* (2013.01); *B01J 2220/49* (2013.01); *G01N 2021/7793* (2013.01)

(58) Field of Classification Search
USPC .......................................................... 436/166
See application file for complete search history.

(56) References Cited

U.S. PATENT DOCUMENTS

| | | | |
|---|---|---|---|
| 3,121,615 | A | 2/1964 | Price |
| 4,034,609 | A | 7/1977 | Fuller |
| 5,064,576 | A | 11/1991 | Suto |
| 5,320,969 | A | 6/1994 | Bauer |
| 6,087,293 | A | 7/2000 | Carnahan |
| 6,877,457 | B1 | 4/2005 | Dick |
| 7,098,253 | B2 | 8/2006 | Rasmussen |
| 7,674,835 | B2 | 3/2010 | Rasmussen |
| 7,683,100 | B2 | 3/2010 | Rasmussen |
| 2008/0063575 | A1 | 3/2008 | Rakow et al. |
| 2008/0163673 | A1 | 7/2008 | Attar |
| 2009/0130412 | A1 | 5/2009 | Hatton |
| 2010/0254890 | A1 | 10/2010 | Yang |
| 2011/0076416 | A1 | 3/2011 | Klipp |
| 2012/0045515 | A1 | 2/2012 | Liu |
| 2012/0144906 | A1 | 6/2012 | Knyrim |

FOREIGN PATENT DOCUMENTS

| | | |
|---|---|---|
| CN | 102046699 A | 5/2011 |
| EP | 0356116 A2 | 2/1990 |
| EP | 1 213 583 | 6/2002 |
| GB | 2 025 047 A | 1/1980 |
| JP | 2007-322345 A | 12/2007 |
| WO | WO 2004/099754 A2 | 11/2004 |
| WO | WO 2012-154314 | 11/2012 |
| WO | WO 2014-078577 | 5/2014 |

OTHER PUBLICATIONS

Daniel, "Moisture Sorption in Commercial Hybrid Maize (*Zea mays* L.) Seeds During Storage at Ambient Tropical Conditions," Research Journal of Seed Science. 2012, vol. 5, No. 1 pp. 32-37.

Greenspan, "Humidity Fixed Points of Binary Saturated Aqueous Solutions," Journal of Research of the National Bureau of Standards-A Physic and Chemistry, Jan.-Feb. 1977, vol. 81A, pp. 89-96.

Hedlin, "Relative Humidities over Saturated Solutions of Nine Salts in the Temperature Range from 0 to 90 °F," International Symposium on Humidity and Moisture Proceedings, 1963; vol. 3, Chapter 31, pp. 519-520.

Mackenzie, Inorganic polymers (geopolymers) containing acid—base indicators as possible colour-change humidity indicators, Materials Letters, 2009, vol. 63, pp. 230-232.

Wu, "Preparation of Perlite-Based Magnesium, Perchlorate Desiccant With Colour Indicator," Talanta, 1994, vol. 41, No. 5, pp. 633-637.

International Search report for PCT International Application No. PCT/US13/70061 dated Mar. 13, 2014, 3 Pages.

Extended European Search Report, EP13855141.1, dated Jul. 12, 2016, 3 pages.

\* cited by examiner

ADJUSTABLE COLORIMETRIC MOISTURE INDICATORS

FIELD

The present disclosure relates to colorimetric moisture indicators that include bis(glyoxime)-transition metal complexes bound to silane-modified solid metal oxide supports. Methods of adjusting the colorimetric response of moisture indicators based on bis(glyoxime)-transition metal complexes bound to solid metal oxide supports are also included.

BACKGROUND

Moisture indicators are used, for example, to determine the amount of moisture or humidity in the vicinity of the indicator. Colorimetric indicators change color upon exposure to moisture or humidity. Current commercialized colorimetric moisture indicators are based on cobalt-containing compounds (e.g., $CoCl_2$). Alternatives to cobalt compounds are currently being pursued due to the potential adverse environmental impact and expense of cobalt. Other compositions, such as gel supports that include iron (II), iron (III), or copper chloride salts have also been used as moisture indicators, but these indicators do not show strong absorptions in the visible electromagnetic spectrum and the moisture-indicating color change is often difficult to detect.

Additionally, many colorimetric moisture indicators exhibit the moisture-sensitive color change at only one or two specific moisture levels, limiting each indicator's application. For example, some colorimetric moisture indicators express a color change at 60% relative humidity. Some applications where moisture indication is used require the indicators to be sensitive to higher or lower levels of relative humidity. Additionally, some compositions comprising inorganic salts are inherently unstable to liquid water contact as the salts can readily be transported out of the system.

SUMMARY

There is a need for economic colorimetric moisture indicators that are not based on cobalt. There is also a need for colorimetric moisture indicators that have a highly visible color change across a wide range of humidity levels, particularly relative humidity levels above 60% relative humidity, and that can change qualitatively and/or quantitatively with a change in humidity, and that are not as susceptible to liquid water transport of system components.

In one aspect of the present disclosure, a composition is provided that includes a solid metal oxide support having surface hydroxyl groups, a silyl-containing compound bound to the solid metal oxide support through a silanol bond with the surface hydroxyl groups, and a bis(glyoxime)-transition metal complex bound to the solid metal oxide support.

In another aspect of the present disclosure, a colorimetric relative humidity-indicating sensor is provided, including a moisture-indicating composition comprising a solid metal oxide support having surface hydroxyl groups, a silyl-containing compound bound to the solid metal oxide support through a silanol bond with the surface hydroxyl groups, and a bis(glyoxime)-transition metal complex bound to the solid metal oxide support, and wherein the optical spectrum of the sensor changes quantitatively according to the relative humidity within the environment within which the sensor is placed.

Finally, in another aspect, a method of adjusting the colorimetric response of a moisture-indicating composition is provided that includes modifying the surface of a solid metal oxide support having surface hydroxyl groups by reacting the surface hydroxyl groups of the solid metal oxide support with a silyl-containing compound to create a silane-modified solid metal oxide support; and bonding a bis(glyoxime)-transition metal complex to the silane-modified solid metal oxide support.

The compositions, sensors, and methods herein can provide highly visible color change across a wide range of humidity levels, particularly relative humidity levels above 60% relative humidity, can provide qualitative and/or quantitative indications of the amount of moisture in the vicinity of the compositions and sensors, and are not as susceptible to liquid water transport of system components as are other moisture-indicating compositions.

The above summary is not intended to describe each disclosed embodiment of every implementation of the present invention. The details of one or more embodiments of the invention are also set forth in the description below. Other features, objects, and advantages of the invention will be apparent from the description and from the claims.

DETAILED DESCRIPTION

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g. 1 to 5 includes 1, 1.5, 2, 2.75, 3, 3.80, 4, and 5) and any range within that range.

As used herein:

"Bis(glyoxime)-transition metal complex" refers to a complex that has two glyoxime moieties complexed to a transition metal; as described further herein, the glyoxime moieties may have alkyl or other groups substituted for hydrogen at the ortho positions.

"Glyoxime" refers to vicinal dioximes of substituted or unsubstituted orthoketones.

"Hue" ranges in value from 0 to 360 (including all numbers in between), and refers to the degree to which a stimulus can be described as similar to or different from stimuli that are described as red, green, and blue and can be calculated using known mathematical techniques described further herein.

"Humidity" and "moisture" are used interchangeably.

"Visible spectroscopic reflection color intensity change" refers to the difference observed between two color states and in some embodiments can be expressed as difference in Hue.

"Visible spectroscopic reflection" refers to measurements of reflections that are typically in the near UV-visible region of the electromagnetic spectrum—from about 350 nm to about 830 nm; it is understood that the actual reflection spectrum of a particular composition may be influenced by solvent, solvation, interference of thin surface coatings, and other environmental parameters such as temperature.

"Optical spectrum" refers to the spectrum of reflected and/or transmitted electromagnetic radiation in the near visible and visible wavelengths from and/or through an object. In some cases, the change in optical spectrum is a visible color change.

"Transition metal" refers to any element or elements having atomic numbers from 21-30, 39-48, 72-80, and 104-112. Exemplary transition metals include zirconium, titanium, rhodium, iridium, platinum, palladium, gold, nickel, copper, and combinations thereof.

Unless otherwise specified, as used herein, all relative humidity values and critical relative humidity values refer to relative humidity and critical relative humidity, respectively, as measured at room temperature (between 22° C. and 28° C.).

Current commercially available humidity indicators rely on inorganic salts such as cobalt (II) chloride to provide visual indication by color intensity change upon exposure to various levels of relative humidity. Recently, cobalt (II) chloride has come under regulatory scrutiny due to environmental concerns. Another problem with the use of cobalt salts for humidity indication is that the color intensity change (for example, blue to pink for cobalt (II) chloride) can be difficult to ascertain, and hence determine the humidity exposure level. Additionally, some compositions comprising inorganic salts may be unstable to liquid water contact as the salts can sometimes be transported out of the system.

Some colorimetric moisture indicators can be placed in close proximity with inorganic hygroscopic salts to shift the applicable range of relative humidity levels in which the indicator changes color. However, use of hygroscopic salts typically shifts the point of color change to lower values of relative humidity, such as relative humidity values below 70%. There remains a need for colorimetric moisture indicators that have a point of color change at higher values of relative humidity, such as relative humidity values of more than 60%, and even more than 70%, relative humidity.

Compositions that include a solid metal oxide support and a bis(glyoxime)-transition metal complex bound to the support can be a useful alternative to cobalt (II) chloride and other inorganic salt-based moisture indicators for colorimetric moisture or humidity determination. Depending upon composition, humidity sensors based on bis(glyoxime)-transition metal complex bound to a solid metal oxide support can be constructed which can quantitatively determine the humidity level of the atmosphere to which the sensor is exposed. Such humidity sensors can also be constructed to provide reversible or irreversible humidity indication. However, many moisture indicators based on bis(glyoxime)-transition metal complex bound to a solid metal oxide support show a sharp color change at relative humidities around 60%. In order to extend the application of moisture indicators based on bis(glyoxime)-transition metal complex bound to a solid metal oxide support, the relative humidity at which the sharp color change occurs must be adjustable across a wide range of humidity conditions.

Provided herein are compositions and sensors based on bis(glyoxime)-transition metal complexes bound to silane-modified solid metal oxide supports. The compositions and sensors can provide qualitative and quantitative detection of moisture across a wide range of relative humidity conditions, such as relative humidities ranging from 50% to 90% at 25° C. Also provided herein are methods of adjusting the colorimetric response of bis(glyoxime)-transition metal complex-based moisture indicators by modifying metal oxide supports using various silanes.

Compositions are provided that include solid metal oxide supports. The solid metal oxide supports can be relatively colorless (e.g. clear, white, etc.) and capable of adsorbing or bonding to chromophoric species. In some embodiments, the provided solid metal oxide supports include oxides of silicon, aluminum, zirconium, titanium, or combinations thereof. Non-limiting examples of suitable metal oxides include silicon oxide, aluminum oxide, tin oxide, zinc oxide, titanium oxide, zirconium oxide, lanthanide ("rare-earth") oxides, and mixtures thereof. Metal oxide supports can also include inorganic polymers (geopolymers) formed by reaction of a reactive solid aluminosilicate source such as a dehydroxylated clay with alkali silicate solution, such as those described in MacKenzie et al., *Materials Letters*, 63, 230-232 (2009). In some embodiments, the provided solid metal oxide supports can include alumina or silica gels, beads, or solid supports. Other exemplary metal oxide supports include zirconium oxide pellets and titanium (IV) oxide pellets. In some embodiments the solid metal oxide supports may comprise beads, pellets, spheres, granules, extrudates, tablets, nanoparticles, fibers, rods, needles, wovens, or nonwovens. In some embodiments, the metal oxide support may be in film form, such as coatings and free-standing films.

Compositions are provided herein with silane-modified metal oxide supports. Silyl-containing compounds having hydroxyl or hydrolyzable groups can react with surface hydroxyl groups of metal oxides and displace the hydroxyl or hydrolyzable groups on the silyl-containing compound to form a covalent —Si—O-M- bond (M is a metal or Si). Through this silanization, the surface of metal oxides can be covered by the silyl-containing groups. The properties of the modified metal oxide surfaces at least partially reflect the characteristics of the silyl-containing groups.

The silane modification of the solid metal oxide support can be accomplished in a variety of known ways. In some embodiments, the solid metal oxide support can be contacted with the silyl-containing compound to form a silane-modified solid metal oxide support. In some embodiments, no more than about 50% of surface hydroxyl groups of the metal oxide support are bound to the silyl-containing compound. In some embodiments, no more than about 40%, 30%, 20%, or 10% of surface hydroxyl groups of the metal oxide support are bound to the silyl-containing compound.

In some embodiments, the solid metal oxide support is mixed into or contacted with a modification composition comprising a silyl-containing compound and an acid. The silyl-containing compound is generally present in the modification composition in amounts ranging from about 0.01% to about 10% (e.g., between 0.1% and 10%, between 0.5% and 5%, or between 1% and 3%) by weight, based on the total weight of the modification composition. The acid may be an organic or inorganic acid. Exemplary organic acids include acetic acid, citric acid, and formic acid. Exemplary inorganic acids include sulfuric acid, hydrochloric acid, and phosphoric acid. The acid will generally be included in the modification composition in an amount between about 0.005 and 10% (e.g., between 0.01 and 10% or between 0.05 and 5%) by weight, based on the total weight of the modification composition. In some embodiments, the modification composition additionally includes water. In some embodiments, the amount of water is between 0.1% and 99.9% (e.g., 0.5% to 95%, 0.5% to 90%, etc.) by weight based on the total weight of the modification composition.

In some embodiments, the solid metal oxide support is mixed into or contacted with a modification composition comprising a silyl-containing compound and a solvent. The silyl-containing compound is generally present in the modification composition in amounts ranging from about 0.1% to about 10% (e.g., between 0.05% and 5% or between 1% and 3%) by weight of the modification composition. Generally, the solvent is organic. Exemplary solvents include toluene, alcohols (e.g., ethanol, isopropanol, etc.), tetrahydrofuran, and hydrocarbon solvents (e.g., hexane, etc.). The solvent will generally be included in the modification composition in an amount between about 0.5% and 99.9% (e.g., between 1% and 99.5%, between 90% and 99%, etc.) by weight, based on the total weight of the modification composition.

In some embodiments, the solid metal oxide support and the silyl-containing compound may be reacted in an oven at elevated temperatures. Oven temperatures can range from 50° C. to 150° C. (e.g., 50° C. to 90° C., 100° C. to 130° C., 110° C. to 120° C., etc.). Oven reaction times can range from 10 hours to 20 hours (e.g., 12 hours to 18 hours or 14 hours to 16 hours). In some embodiments, the solid metal oxide support and the silyl-containing compound may be reacted through vapor deposition.

Various silyl-containing compounds can be used to modify the solid metal oxide support. In some embodiments, the silyl-containing compound is of Formula (I):

$$R^1-Si(R^2)_{3-x}(R^3)_x \qquad (I)$$

wherein $R^1$ is an alkyl, fluoroalkyl, alkyl substituted with an amino, aryl, aralkyl, or alkaryl group; each $R^2$ is independently hydroxyl or a hydrolyzable group; each $R^3$ is independently a non-hydrolyzable group; and x is an integer equal to 0, 1, or 2. In some embodiments, the silyl-containing compound is of Formula (II)

$$(R^3)_x(R^2)_{3-x}Si-R^4-Si(R^2)_{3-x}(R^3)_x \qquad (II)$$

wherein $R^4$ is an alkylene, arylene, or a combination thereof; each $R^2$ is independently hydroxyl or a hydrolyzable group; each $R^3$ is independently a non-hydrolyzable group; and x is an integer equal to 0, 1, or 2.

In some embodiments, the hydrolyzable group can include alkoxy, aryloxy, acyloxy, halo, $-N(R^5)_2$, or $-NH-Si(R^5)_3$ where $R^5$ is alkyl and the non-hydrolyzable group can include alkyl, aryl, aralkyl, or alkaryl. In some embodiments, the non-hydrolyzable group is alkyl, aryl, aralkyl, or alkaryl.

"Hydrolyzable group" refers to one of more groups bonded to a silicon atom in a silyl group that can react with water having a pH of 1 to 10 under conditions of atmospheric pressure. The hydrolyzable group is often converted to a hydroxyl group when it reacts. The hydroxyl group often undergoes further reactions such as reactions with hydroxyl groups on a surface of a metal oxide support. Exemplary hydrolyzable groups include, but are not limited to, alkoxy, acyloxy, halo, $-N(R^5)_2$, or $-NH-Si(R^5)_3$ where $R^5$ is alkyl.

"Non-hydrolyzable group" refers to one of more groups bonded to a silicon atom in a silyl group that can react with water having a pH of 1 to 10 under conditions of atmospheric pressure. These groups typically do not undergo reactions such as reactions with hydroxyl groups on a surface of a metal oxide support. Exemplary non-hydrolyzable groups include, but are not limited to alkyl, aryl, aralkyl, and alkaryl.

"Alkyl" refers to a monovalent group that is a radical of an alkane. The alkyl group can have 1 to 40 carbon atoms. The alkyl group can be linear, branched, cyclic, or a combination thereof. When the alkyl is linear, it can have 1 to 40 carbon atoms, 1 to 30 carbon atoms, 1 to 20 carbon atoms, or 1 to 10 carbon atoms. When the alkyl is branched or cyclic, it can have 3 to 40 carbon atoms, 3 to 30 carbon atoms, 3 to 20 carbon atoms, or 3 to 10 carbon atoms.

"Alkylene" refers to a divalent group that is a radical of an alkane. The alkylene group can have 1 to 40 carbon atoms. The alkylene group can be linear, branched, cyclic, or a combination thereof. When the alkylene is linear, it can have 1 to 40 carbon atoms, 1 to 30 carbon atoms, 1 to 20 carbon atoms, or 1 to 10 carbon atoms. When the alkylene is branched or cyclic, it can have 3 to 40 carbon atoms, 3 to 30 carbon atoms, 3 to 20 carbon atoms, or 3 to 10 carbon atoms.

"Aryl" refers to a monovalent group that is a radical of an aromatic carbocyclic compound. The aryl group has at least one aromatic carbocyclic ring and can have 1 to 5 optional rings that are connected to or fused to the aromatic carbocyclic ring. The additional rings can be aromatic, aliphatic, or a combination thereof. The aryl group usually has 5 to 20 carbon atoms. In some embodiments, the aryl group is phenyl.

"Arylene" refers to a divalent group that is a radical of an aromatic carbocyclic compound. The arylene group has at least one aromatic carbocyclic ring and can have 1 to 5 optional rings that are connected to or fused to the aromatic carbocyclic ring. The additional rings can be aromatic, aliphatic, or a combination thereof. The aryl group usually has 5 to 20 carbon atoms. In some embodiments, the arylene is phenylene.

"Alkoxy" refers to a monovalent group of formula —OR where R is an alkyl as defined above. In some embodiments, the alkoxy is methoxy, ethoxy, or propoxy.

"Fluoroalkyl" refers to an alkyl having at least one hydrogen atom replaced with a fluoro.

"Aryloxy" refers to a monovalent group of formula —OAr where Ar is an aryl group.

"Aryloxy" refers to a monovalent group of formula —O(CO)—Ra where Ra is an alkyl, aryl, aralkyl, or alkaryl. In some embodiments, the acyloxy is —O(CO)CH₃ (acetoxy).

"Halo" refers to a monovalent group that is a radical of a halogen atom. The halo can be fluoro, chloro, bromo, or iodo. In some embodiments, the halo is chloro.

"Aralkyl" refers to an alkyl group substituted with at least one aryl group. The aralkyl group contains 6 to 40 carbon atoms. The aralkyl group often contains an alkyl group having 1 to 20 carbon atoms and an aryl group having 5 to 20 carbon atoms.

"Alkaryl" refers to an aryl group substituted with at least one alkyl group. The aralkyl group contains 6 to 40 carbon atoms. The aralkyl group often contains an aryl group having 5 to 20 carbon atoms and an alkyl group having 1 to 20 carbon atoms.

"Amino" refers to a monovalent group of formula —N($R^6$) where $R^6$ is hydrogen or alkyl.

The specific silyl-containing compound can be chosen based on the desired relative humidity at which the final moisture indicating composition should undergo sharp color change. The characteristics of the silyl-containing compound (hydrophobic, hydrophilic, etc) generally correlate to the relative humidity at which the final moisture-indicating composition shows significant color change. One silyl-containing compound or mixtures of two or more silyl-containing compounds can be used to modify the solid metal oxide support and adjust the color response of the moisture-indicating compositions. In some embodiments, the silyl-containing compound may be hydrophobic. For example, hydrophobic compounds of Formula (I), include compounds where group $R^1$ plus any non-hydrolyzable group $R^3$ are hydrophobic. As another example, hydrophobic compounds of Formula (II), include compounds where group $R^4$ plus any non-hydrolyzable group $R^3$ are hydrophobic.

Exemplary silyl-containing compounds that may be bound to the solid metal oxide support include, but are not limited to, acetoxytrimethylsilane, t-butyldimethylchlorosilane, cyclohexylmethyldichlorosilane, cylcohexylmethyldimethoxysilane, 1,3-di-n-butyltetramethylsilazane, diethoxydimethylsilane, (diethylamino)trimethylsilane, (dimethylamino)trimethylsilane, diisopropyldichlorosilane, diisopropyldimethoxysilane, dimethyldichlorosilane, dimethyldiethoxysilane, dimethyldimethoxysilane, diphenyldichlorosilane, diphenyldiethoxysilane, diphenyldimethoxysilane, diphenylmethyldichlorosilane, dodecyltrichlorosilane, ethyltriacetoxysilane, ethyltrichlorosilane, ethyltrimethoxysilane, hexadecyltrimethoxysilane, hexamethyldisilazane, hexyltrimethoxysilane, isobutyltrimethoxysilane, isooctyltriethoxysilane, isooctyltrimethoxysilane, isobutyltriethoxysilane, methyltriacetoxysilane, methyltrichlorosilane, methyltriethoxysilane, methyltrimethoxysilane, n-octadecyldimethylchlorosilane, n-octadecyltrichlorosilane, n-octadecyltrimethoxysilane, n-octyltrichlorosilane, n-octyltriethoxysilane, n-octyltrimethoxysilane, phenethyltrimethoxysilane, phenyldimethylchlorosilane, phenylmethyldimethoxysilane, phenyltrichlorosilane, phenyldimethylchlorosilane, phenyltriethoxysilane, phenyltrimethoxysilane, n-propyltrichlorosilane, n-propyltriethoxysilane, n-propyltrimethoxysilane, trimethylchlorosilane, trimethylethoxysilane, trimethylmethoxysilane, 1H,1H,2H,2H-perfluoroctyldimethylchlorosilane, (3-aminopropyl)triethoxysilane, bis(triethyoxysilyl)ethane, and 1(triethoxysilyl)-2-(diethoxymethylsilyl)-ethane.

Compositions are provided herein with bis(glyoxime)-transition metal complexes, bound to silane-modified metal oxide supports. By bound it is meant that there is an attractive interaction between the bis(glyoxime)-transition metal complex and the solid metal oxide support. The attractive interaction can include covalent bonds, ionic bonds, dative bonds, metallic bonds, hydrogen bonds, van der Waals forces, electrostatic forces, chemisorption, physisorption, or any other interaction that attracts the bis(glyoxime)-transition metal complex to the solid metal oxide support. For example, when a bis(glyoxime)-transition metal complex that is insoluble in water or slightly soluble in water is bound to a solid support, it is typically not removed by successive or continuous rinsing with water. In some embodiments, the attractive interaction includes hydrogen bonds.

The bis(glyoxime)-transition metal complex includes two glyoxime moieties that form a complex with transition metals. The bis(glyoxime)-transition metal complex generally has the structure of Formula (III):

(III)

wherein:

M is a transition metal; and

R is independently selected from the groups comprising alkyl, such as ethyl and methyl; aryl, such as phenyl; thioaryl, such as thiophenyl; and a heterocyclic group, such as piperidine and morpholine.

Common glyoxime moieties include dialkylglyoximes such as, for example, dimethylglyoxime and diethylglyoxime. Common glyoximes that may also be useful in the provided compositions include diphenylglyoxime and bis(thiophenyl)glyoxime. Additionally, morpholine and piperidine have been reacted with anti-chloroglyoxime to give morpholineglyoxime and piperidineglyoxime. Since the transition metal ion complexes with the heteroatoms of the glyoxime species (nitrogen and oxygen, for example) it is contemplated that other substituents on the glyoxime molecule may be useful compositions if they do not interfere with the ability of the two glyoxime moieties to complex with a transition metal ion. When complexed, the bis(glyoxime)-transition metal complex typically has a square planar configuration. In some embodiments, the bis(glyoxime)-transition metal complex can include ions of rhodium, iridium, platinum, palladium, gold, nickel or copper which are well known by those of ordinary skill in the art to form square planar coordination complexes with glyoxime moieties like dimethylglyoxime. An exemplary bis(glyoxime)-transition metal complex for use in the moisture-indicating media is nickel dimethylglyoxime. A structure of an exemplary nickel bis(dimethylglyoxime) complex, bis-(dimethylglyoximato) nickel (II), is shown in Formula (IV) below:

(IV)

The color of the compositions described herein may be observed visually with the human eye, or with the assistance of measuring devices such as a spectrophotometer or a colorimeter. The amount of moisture to which the colorimetric moisture-indicating sensor is exposed can be measured spectroscopically, for example, by reflection. Since the provided colorimetric moisture-indicating compositions are solid, the change in color can be measured by reflecting light off of the surface of the solid and measuring the loss of intensity from wavelengths absorbed by the surface. In some embodiments, the absorbance at a given wavelength can be measured using an optics spectroscopy system that is configured for reflection spectroscopy. An exemplary optics spectroscopy system suitable for this measurement is Model Jaz-EL350, available from Ocean Optics, Dunedin, Fla. Typically, a spectrum from a white piece of paper or white powders can be used as a reference spectrum when measuring reflection intensity.

In some embodiments, the visible spectroscopic reflection intensity in the wavelength range of 460 nm to 560 nm and color can be expressed as the Hue. Hue may be quantitatively related to the level of moisture in the environment within which the composition is located, and may be determined by converting a measured reflection spectrum to Hue using known mathematical techniques as described further herein. In some embodiments, the color, Hue, reflection spectrum, or transmission spectrum of the moisture-indicating composition is quantitatively related to the level of moisture (humidity or relative humidity) in the environment in which the moisture-indicating composition is located. By quantitatively it is meant that the reflection intensity in the wavelength range of 460 nm to 560 nm and the Hue number, expressed by color, has a one-to-one correlation to the amount of humidity or relative humidity. The environment within which the moisture-indicating composition is located can be an area or volume surrounding the moisture-indicating composition, including, for example, the area, volume, and/or atmosphere in contact with the moisture-indicating composition. In some embodiments, the color, Hue, reflection spectrum, or transmission spectrum of the moisture-indicating composition is directly related to the level of moisture (humidity or relative humidity) in an environment. By directly related, it is meant that the property gives information about the level of moisture in the environment within which the moisture-indicating composition is located. This information may be approximate, or may be quantitatively related to the level of moisture in the environment within which the moisture-indicating composition is located. In some embodiments where color is visually observed to determine the level of moisture, the moisture-indicating composition will exhibit a distinct color change with varying moisture conditions. For example, the moisture-indicating composition may exhibit two different colors at two different levels of relative humidity, such as appearing green at a relative humidity of 30% and appearing pink at a relative humidity of 70% at 25° C.

The compositions can be used as moisture-indicating compositions in any environment or space, including both enclosed spaces or volumes and unenclosed spaces or volumes. Exemplary environments include enclosed containers, packaging, rooms, etc. In some embodiments, the conditions of temperature and pressure within the environment will be homogeneous. In some embodiments, the conditions of temperature and pressure within the environment will not be homogeneous.

In some embodiments, the compositions described herein can exhibit extended relative humidity response ranges as compared to moisture-indicating compositions based on bis(glyoxime)-transition metal complexes bound to non-silanized solid metal oxide supports. In some embodiments, the g compositions described herein quantitatively change color, Hue, reflection spectrum, or transmission spectrum at relative humidities ranging from about 50% to about 90% relative humidity at 25° C. In some embodiments, the compositions quantitatively change color, reflection spectrum, or transmission spectrum at relative humidities ranging from about 60% to about 80% relative humidity at 25° C. In some embodiments, the compositions quantitatively change color, reflection spectrum, or transmission spectrum at relative humidities of about 50%, 60%, 70%, 80%, and 90% at 25° C.

In some embodiments, the colorimetric moisture-indicating compositions can be irreversible. By irreversible, it is meant that when the composition is exposed to one set of humidity conditions it has an original value associated with a specific optical spectrum (or Hue, or color). When the set of humidity conditions is changed, the composition changes color to give a different, second value associated with a specific optical spectrum (or Hue, or color). And, when the composition is returned to the initial set of humidity conditions, the optical spectrum (or Hue, or color) does not return to the original optical spectrum (or Hue, or color).

In some embodiments, the colorimetric moisture-indicating compositions can be reversible. By reversible it is meant that when the composition is exposed to one set of humidity conditions it has an original value associated with a specific optical spectrum (or Hue, or color). When the set of humidity conditions is changed, the composition changes color to give a different, second value associated with a specific optical spectrum (or Hue, or color); and, finally, when the composition is returned to the initial set of humidity conditions, the composition changes again, resulting in a third value associated with a specific optical spectrum (or Hue, or color). That resulting third value returns to approximately the original value. In some embodiments, the moisture-indicating compositions will exhibit complete reversibility. Such reversible moisture-indicating compositions substantially return to the original value of the specific optical spectrum (or Hue, or color) when re-exposed to the initial set of humidity conditions. Thus, for completely reversible moisture-indicating compositions, the third value of the specific optical spectrum (or Hue, or color) is substantially equivalent to the original value of the specific optical spectrum (or Hue, or color). In other embodiments, the moisture-indicating compositions will exhibit partial reversibility, i.e., when the composition is returned to the initial set of humidity conditions, the resulting third value of the specific optical spectrum (or Hue, or color) is closer to the original value than to the second value. For example, when the solid metal oxide support is aluminum oxide, silicon oxide, or a combination thereof, and when the bis(glyoxime)-transition metal complex includes nickel and two dimethylglyoxime moieties (the complex shown in Formula (II)) a reversible moisture-indicating composition can be formed.

In some embodiments, the color changes are easily detectable with the human eye. In these embodiments, the human eye can detect the difference between the original value and the second value of the color (or Hue), as well as the difference between the second value and the third value of the color (or Hue). Thus, in some embodiments the difference between the original Hue number and the second Hue number, or the difference between the second Hue number and the third Hue number is at least 15, in some embodiments at least 30, and in some embodiments at least 60. In some color ranges, such as between Hue numbers of 0 and 60, or Hue numbers of 300 and 360, smaller differences in Hue are detectable with the human eye. In other color ranges, such as between Hue numbers of 60 and 300, only larger differences in Hue number may be detectable with the human eye. It is not necessary that the difference between the original value and the third value of the color (or Hue), if any, is detectable by the human eye.

Using the above-identified compositions, colorimetric moisture-indicating sensors can be constructed. The moisture-indicating compositions may be made into a multimedia construction in combination with other media and/or containment devices. Exemplary multimedia constructions can include loose-packed indicator constructions (e.g., particles or fibers contained in a vial, packed in a tube, or wrapped in a flexible fabric), loose, non-packed indicator constructions (e.g., physically entangled moisture-indicating media in a fibrous web, such as particle-loaded webs), multilayer constructions (e.g., indicator films on or between additional material layers which may have varying degrees of fluid permeability, or indicator particles or fibers sandwiched between containment layers), or partially embedded or encapsulated constructions (e.g., particles or fibers partially embedded in a polymer, such as an adhesive-coated film or fiber; composites, such as an articulated bulk shape, film, or fiber). In some embodiments, moisture-indicating media particles or fibers may also be contained in a porous matrix. In some embodiments, the moisture-indicating composition may be dispersed or dissolved in a solvent.

In some embodiments, the moisture-indicating compositions can be attached to, deposited on, physically entangled in, and/or embedded in secondary supports. The secondary supports can be one dimensional (e.g., fiber), two dimensional (e.g., planar substrates such as paper, glass, or polymer films), and three dimensional (e.g., fiber network, sponge structures). The moisture-indicating compositions can be attached to the secondary supports by physical adsorption of the mixture to the secondary supports or using adhesives (such as pressure sensitive adhesives) or binding polymers (such as polyvinyl alcohol). In some embodiments, the moisture-indicating compositions can be deposited on backing material or carrier material to create moisture-indicating sensors in the form of cards and tapes according to conventional methods known in the art. Exemplary backing materials and carrier materials include those made of paper, kraft papers, polyethylene, polypropylene, polyester or composites of any of these materials. In some embodiments, the side of the backing materials and carrier materials opposite the deposited moisture-indicating compositions can be coated with release agents such as fluorochemicals or silicones. Exemplary tapes may comprise acrylic, urethane, and silicone polymers. In some embodiments, the sensor is structured such that the moisture-indicating composition is in fluid communication with the surrounding environment.

In some embodiments, the compositions can be inserted between two secondary supports. In such cases, one of the secondary supports may be visibly transparent enough to allow visual observation the color change of indicators. At least one of the secondary supports should allow the transfer of humidity to the moisture-indicating composition. In some embodiments, both of the secondary supports are impermeable to particles.

In some embodiments, the compositions can be contained within transparent or semi-transparent vials or containers that have caps. The caps may optionally comprise filtering layers that are impermeable to particles, but that allow the transfer of humidity across the filters.

Also provided is a method of adjusting the colorimetric response of moisture indicators based on bis(glyoxime)-transition metal complexes bound to solid metal oxide supports. The method can comprise the steps of modifying the surface of a solid metal oxide support having surface hydroxyl groups by reacting the surface hydroxyl groups of the solid metal oxide support with a silyl-containing compound to create a modified solid metal oxide support, and bonding a bis(glyoxime)-transition metal complex to the modified solid metal oxide support to create a moisture-indicating composition. Exemplary solid metal oxide supports, silyl-containing compounds and bis(glyoxime)-transition metal complexes include those described herein. Exemplary methods for modifying the surface of a solid metal oxide support having surface hydroxyl groups by reacting the surface hydroxyl groups of the solid metal oxide support with a silyl-containing compound to create a modified solid metal oxide support include those described herein.

In some embodiments, the moisture-indicating compositions will exhibit a sharp color change at a relative humidity that is different from the relative humidity at which a sharp color change occurs for a similar moisture-indicating composition comprising the same bis(glyoxime)-transition metal complexes bound to the same, but non-silanized, metal oxide support. The shift in color or optical spectrum change (as compared to the color or optical spectrum change exhibited by the same bis(glyoxime)-transition metal complexes bound to the same, but non-silanized, metal oxide support) depends on the type of silyl-containing compound used. In general, the modification of the metal oxide support with silyl-containing compounds results in compositions that exhibit color or optical spectrum changes at higher relative humidities than a similar moisture-indicating composition comprising the same bis(glyoxime)-transition metal complexes bound to the same, but non-silanized, metal oxide support. In some embodiments the modification of the metal oxide support with silyl-containing compounds typically shifts the point of color change to higher values of relative humidity, such as relative humidity values above 60%.

Also provided is a method of detecting moisture. The method includes providing a composition that includes a silane-modified solid metal oxide support and a bis(glyoxime)-transition metal complex bound to the support and then exposing the composition to a moist atmosphere. The provided method further includes observing the color of the composition and/or measuring the visible spectroscopic reflection spectrum of the composition after exposing it to a moist atmosphere.

Following are exemplary embodiments of a bis(glyoxime)-transition metal complexes and moisture indicators made therewith according to aspects of the present invention.

Embodiment 1 is a composition comprising a solid metal oxide support having surface hydroxyl groups, a silyl-containing compound bound to the solid metal oxide support through a silanol bond with the surface hydroxyl groups, and a bis(glyoxime)-transition metal complex bound to the solid metal oxide support.

Embodiment 2 is a composition according to embodiment 1, wherein the silyl-containing compound is of Formula (I)

$$R^1—Si(R^2)_{3-x}(R^3)_x \quad (I)$$

wherein

$R^1$ is an alkyl, fluoroalkyl, alkyl substituted with an amino group, aryl, aralkyl, or alkaryl;

each $R^2$ is independently hydroxyl or a hydrolyzable group;

each $R^3$ is independently a non-hydrolyzable group; and x is an integer equal to 0, 1, or 2.

Embodiment 3 is a composition according to embodiment 1, wherein the silyl-containing compound is of Formula (II)

$$(R^3)_x(R^2)_{3-x}Si-R^4-Si(R^2)_{3-x}(R^3)_x \quad (II)$$

wherein $R^4$ is an alkylene, arylene, or a combination thereof;

each $R^2$ is independently hydroxyl or a hydrolyzable group;

each $R^3$ is independently a non-hydrolyzable group; and x is an integer equal to 0, 1, or 2.

Embodiment 4 is a compositions according to any one of embodiments 2-3, wherein the hydrolyzable group is alkoxy, aryloxy, acyloxy, halo, —N(R$^5$)$_2$, or —NH—Si(R$^5$)$_3$ where R$^5$ is alkyl.

Embodiment 5 is a compositions according to any one of embodiments 2-4, wherein the non-hydrolyzable group is alkyl, aryl, aralkyl, or alkaryl.

Embodiment 6 is a composition according to any of the preceding embodiments, wherein the silyl-containing compound is selected from the group consisting of diethoxydimethylsilane, hexamethyldisilazane, n-octadecyltrichlorosilane, 1H,1H,2H,2H-perfluoroctyldimethylchlorosilane, and (3-aminopropyl)triethoxysilane.

Embodiment 7 is a composition according to any of the preceding embodiments, wherein no more than about 50% of surface hydroxyl groups of the support are bound to the silyl-containing compound.

Embodiment 8 is a composition according to any of the preceding embodiments, wherein the solid metal oxide support comprises an oxide of aluminum, silicon, or a combination thereof.

Embodiment 9 is a composition according to any of the preceding embodiments, wherein the solid metal oxide comprises an oxide of zirconium, titanium, or a combination thereof.

Embodiment 10 is a composition according to any of the preceding embodiments, wherein the transition metal in the bis(glyoxime)-transition metal complex comprises rhodium, iridium, platinum, palladium, gold, nickel, copper, or a combination thereof.

Embodiment 11 is a composition according to any of the preceding embodiments, wherein the bis(glyoxime)-transition metal complex comprises bis(dimethylglyoximato)-nickel(II).

Embodiment 12 is a composition according to any one of the preceding embodiments, wherein the composition quantitatively changes optical spectrum at relative humidities ranging from about 50% to about 90% relative humidity at 25° C.

Embodiment 13 is a composition according to any one the preceding embodiments, wherein the composition quantitatively changes optical spectrum at relative humidities ranging from about 60% to about 80% relative humidity at 25° C.

Embodiment 14 is a colorimetric relative humidity-indicating sensor comprising a moisture-indicating composition comprising a solid metal oxide support having surface hydroxyl groups, a silyl-containing compound bound to the solid metal oxide support through a silanol bond with the surface hydroxyl groups, and a bis(glyoxime)-transition metal complex bound to the solid metal oxide support; and wherein the optical spectrum of the sensor changes quantitatively according to the relative humidity within the environment within which the sensor is placed.

Embodiment 15 is a sensor according to embodiment 14, wherein the silyl-containing compound is of Formula (I)

$$R^1-Si(R^2)_{3-x}(R^3)_x \quad (I)$$

wherein

$R^1$ is an alkyl, fluoroalkyl, alkyl substituted with an amino, aryl, aralkyl, or alkaryl group;

each $R^2$ is independently hydroxyl or a hydrolyzable group;

each $R^3$ is independently a non-hydrolyzable group; and x is an integer equal to 0, 1, or 2.

Embodiment 16 is a sensor according to embodiment 14, wherein the silyl-containing compound is of Formula (II)

$$(R^3)_x(R^2)_{3-x}Si-R^4-Si(R^2)_{3-x}(R^3)_x \quad (II)$$

wherein $R^4$ is an alkylene, arylene, or a combination thereof;

each $R^2$ is independently hydroxyl or a hydrolyzable group;

each $R^3$ is independently a non-hydrolyzable group; and x is an integer equal to 0, 1, or 2.

Embodiment 17 is a sensor according to any one of embodiments 15-16, wherein the hydrolyzable group is alkoxy, aryloxy, acyloxy, halo, —N(R$^5$)$_2$, or —NH—Si(R$^5$)$_3$ where R$^5$ is alkyl.

Embodiment 18 is a sensor according to any one of embodiments 15-17, wherein the non-hydrolyzable group is alkyl, aryl, aralkyl, or alkaryl.

Embodiment 19 is a sensor according to any of embodiments 14-18, wherein no more than about 50% of surface hydroxyl groups of the support are bound to the silyl-containing compound.

Embodiment 20 is a sensor according to any one of embodiments 14-19, wherein the solid metal oxide support comprises an oxide of aluminum, silicon, or a combination thereof.

Embodiment 21 is a sensor according to any one of embodiments 14-20, wherein the bis(glyoxime)-transition metal complex comprises bis(dimethylglyoximato)-nickel (II).

Embodiment 22 is a sensor according to any one of embodiments 14-21, wherein the sensor quantitatively changes optical spectrum at relative humidities ranging from about 50% to about 90% relative humidity at 25° C.

Embodiment 23 is a sensor according to any one of embodiments 14-22, wherein the sensor quantitatively changes optical spectrum at relative humidities ranging from about 60% to about 80% relative humidity at 25° C.

Embodiment 24 is a sensor according to any one of embodiments 14-23, wherein the moisture-indicating composition is deposited on a backing material.

Embodiment 25 is a method of adjusting the colorimetric response of a moisture-indicating composition comprising:

modifying the surface of a solid metal oxide support having surface hydroxyl groups by reacting the surface hydroxyl groups of the solid metal oxide support with a silyl-containing compound to create a modified solid metal oxide support; and bonding a bis(glyoxime)-transition metal complex to the modified solid metal oxide support to create a moisture-indicating composition.

Embodiment 26 is a method according to embodiment 25, wherein the silyl-containing compound is of Formula (I)

$$R^1-Si(R^2)_{3-x}(R^3)_x \quad (I)$$

wherein $R^1$ is an alkyl, fluoroalkyl, alkyl substituted with an amino, aryl, aralkyl, or alkaryl group;

each $R^2$ is independently hydroxyl or a hydrolyzable group;

each R³ is independently a non-hydrolyzable group; and x is an integer equal to 0, 1, or 2.

Embodiment 27 is a method according to embodiment 25, wherein the silyl-containing compound is of Formula (II)

$$(R^3)_x(R^2)_{3-x}Si-R^4-Si(R^2)_{3-x}(R^3)_x \qquad (II)$$

wherein

R⁴ is an alkylene, arylene, or a combination thereof;

each R² is independently hydroxyl or a hydrolyzable group;

each R³ is independently a non-hydrolyzable group; and x is an integer equal to 0, 1, or 2.

Embodiment 28 is a method according to any one of embodiments 26-27, wherein the hydrolyzable group is alkoxy, aryloxy, acyloxy, halo, —N(R⁵)₂, or —NH—Si(R⁵)₃ where R⁵ is alkyl.

Embodiment 29 is a method according to any one of embodiments 26-28, wherein the non-hydrolyzable group is alkyl, aryl, aralkyl, or alkaryl.

Embodiment 30 is a method according to any of embodiments 25-29, wherein no more than about 50% of surface hydroxyl groups of the support are bound to the silyl-containing compound.

Embodiment 31 is a method according to any one of embodiments 25-30, wherein the solid metal oxide support comprises an oxide of aluminum, silicon, or a combination thereof.

Embodiment 32 is a method according to any one of embodiments 25-31, wherein the solid metal oxide comprises an oxide of zirconium, titanium, or a combination thereof.

Embodiment 33 is a method according to any one of embodiments 25-32, wherein the bis(glyoxime)-transition metal complex comprises bis(dimethylglyoximato)-nickel (II).

Embodiment 34 is a method according to any one of embodiments 25-33, wherein the moisture-indicating composition quantitatively changes optical spectrum at relative humidities ranging from about 50% to about 90% relative humidity at 25° C.

Embodiment 35 is a method according to any one of embodiments 25-34, wherein the moisture-indicating composition quantitatively changes optical spectrum at relative humidities ranging from about 60% to about 80% relative humidity at 25° C.

Embodiment 36 is a method of detecting moisture comprising providing a composition comprising a silane-modified solid metal oxide support and a bis(glyoxime)-transition metal complex bound to the support; exposing the composition to a moist atmosphere; and determining the level of moisture within the moist atmosphere.

Embodiment 37 is a method according to embodiment 36, wherein determining the level of moisture comprises visually observing the color of the composition after exposing it to a moist atmosphere.

Embodiment 38 is a method according to any one of embodiments 36-37, wherein determining the level of moisture comprises measuring the visible spectroscopic reflection spectrum of the composition after exposing it to a moist atmosphere.

Embodiment 39 is a colorimetric moisture-indicating card comprising the composition of any one of Embodiments 1-13.

Objects and advantages of this invention are further illustrated by the following examples, but the particular materials and amounts thereof recited in these examples, as well as other conditions and details, should not be construed to unduly limit this invention.

EXAMPLES

All percentages and ratios are by weight unless otherwise specified.

The compositions are shown in these examples as: transition metal/(bis)glyoxime/solid metal oxide support (e.g., Ni²⁺/dimethylglyoxime/SiO₂ microbeads). When the metal oxide support was modified with silyl-containing groups, the modifier is included such that the compositions are shown as: transition metal/(bis)glyoxime/modifier-solid metal oxide support (e.g., Ni²⁺/dimethylglyoxime/DEDMS-modified SiO₂ microbeads). As used herein, "alumina spheres" may also be referred to as "alumina beads." The terms "beads" and "microbeads" are used interchangeably.

As used in these examples, each change in the level of relative humidity indicates a step change in 10% increments, unless specified otherwise.

Test Methods and Preparatory Methods
Humidity Controlled Air

A test assembly was used to humidify and deliver humidified air to a mixing chamber where it was mixed with dry air to provide humidified air controlled to the step changes in percent relative humidity (% RH) detailed in the examples. The controlled humidity air (% RH±1%) was delivered to a test chamber where a moisture-indicating composition was tested.

Air was humidified in a water jacketed 500 mL 3-neck round-bottom flask controlled to 35.5° C. or 29° C. with a heating/cooling circulator (Model 1160S from VWR). The flask contained about 250 mL of distilled water. Dry air was flowed through tubing from a flow meter into the inlet neck of the flask to evaporate water. The middle neck was fitted with a thermometer. The exit neck of the flask was connected by tubing to the inlet of a 3-neck flask that served as a mixing chamber. Dry air was flowed into the mixing chamber and mixed with the humid air to the desired relative humidity for testing. The humidified air was then flowed into a test chamber. Gas flow regulators (Matheson, Basking Ridge, N.J.) were used to control the flow of the air streams through the apparatus at about 7.5 liters/minute. Tubing under the trade mark TEFLON was used throughout the system. The humidity and temperature were monitored and recorded with a humidity meter (iTHX-M Humidity Meter, Omega Engineering Inc., Stamford, Conn.). The measured temperature was usually around 23±0.7° C.

The test chamber was prepared with two glass plates (approximately 7.5 cm×10 cm) separated by two rubber sheets (approximately 7.5 cm×10 cm×0.7 cm) that had 2.5 cm×7.5 cm cutouts in the center forming a chamber. A 0.6 cm opening on the top glass plate at one end of the chamber was used to deliver controlled humidity air to the test chamber and air flowed out of a second 0.6 cm opening on the other end of chamber to the humidity meter.

Preparation of an Indicator Tape for Testing

The compositions (e.g., Ni²⁺/dimethylglyoxime/SiO₂ microbeads, Ni²⁺/dimethylglyoxime/DEDMS-modified SiO₂ microbeads, etc.) were tested for optoelectronic measurements in the form of an indicator tape. The tape was prepared by placing approximately 20 mg of a moisture-indicating composition on a 1 cm×1 cm square piece of #1 Whatman filter paper. The moisture-indicating composition was covered by a 1 cm by 3 cm strip of clear adhesive tape (SCOTCH® Premium Transparent Film Tape 600 Clear, 3M Company, St. Paul, Minn.) and the outer edges of the paper were sealed to the tape to encapsulate the moisture-indicating composition to form the indicator tape. The exposed adhesive portions of the tape were covered with a plastic film to facilitate handling. The indicator tape was suspended across the opening on the top rubber sheet with the paper side facing the inside of the chamber and the tape side against the top glass plate so that controlled humidity air flowing into the chamber contacted the moisture-indicating composition through the permeable filter paper.

Testing of Moisture-Indicating Compositions (Beads)

Moisture-indicating compositions (e.g. $Ni^{2+}$/dimethylglyoxime/$Al_2O_3$ beads, $Ni^{2+}$/dimethylglyoxime/HDMS-modified $Al_2O_3$ beads, etc.) were suspended between #1 Whatman filter paper in the test chamber and the top glass place without using a clear adhesive tape. The filter paper, cut to 1 cm by 4 cm strip of paper and crafted to hold the beads, was suspended across the opening on the top rubber sheet of the test chamber. Controlled humidity air flowing into the chamber contacted the moisture-indicating composition through the permeable filter paper.

Optoelectronic Measurement Method

The color changes of moisture-indicating compositions were observed using a spectroscopy system. One end of a reflection optical probe (Model QR400-7-UV-VIS, obtained from Ocean Optics; Dunedin, Fla.) was connected to a light source (Model HL-2000-FHSA, Ocean Optics) and the other to a spectrometer (Jaz-EL350, Ocean Optics). The probe was located above the moisture-indicating composition in the test chamber to measure reflection spectra. A spectrum from white alumina microbeads (AG™7, 100-200 mesh microbeads, BioRad Laboratories) was taken for a reference spectrum for reflection intensity. The wavelength range of spectra was from 340.58 nm to 1031.1 nm. A plot of Reflection Intensity (%) vs Wavelength was generated for each % RH test condition.

The obtained reflection spectrum was converted to color, i.e., RGB color space as follows. The measured reflection spectrum was constructed to International Commission on Illumination (or "CIE") XYZ color space using color matching the CIE 1931 2° Standard Observer function. The CIE XYZ color space was linear transformed to National Television System Committee (NTSC) RGB space using NTSC color space chromaticity coordinates ($x_R$=0.67, $y_R$=0.33. $x_G$=0.21, $y_G$=0.71, $x_B$=0.14, $y_B$=0.08). Then, Hue, one of the main properties of a color, was computed from RGB values. Hue, as defined above, is the degree to which a stimulus can be described as similar to or different from stimuli that are described as red, green, and blue. The color can be correlated to a location (Hue) in the color wheel from 0 degree to 360 degree. The color at 0 degree is equal to that at 360 degrees. When color changes from 10 degree to 350 degree, 350 degree was displayed as −10 degree (=350-360) for showing continuous color change. All mathematical processing was done by a customized LABVIEW program (software available from National Instruments of Austin, Tex.). The conversion from spectra to Hue was confirmed by measuring spectra from color printed papers with known Hue, calculating Hue from spectra and comparing Hue from spectra with the known Hue of color printed papers. Hues from the spectra were consistent with the known Hues of color printed papers.

Controlled humidity levels at 23° C. and the corresponding reflection spectra were acquired every 10 seconds simultaneously. When Hue from reflection spectra was stabilized at a certain value, i.e., no further change occurred, the next humidity level was applied step by step.

Materials

Acetic acid—refers to a 0.01 M aqueous solution of acetic acid, prepared from dilution of glacial acetic acid obtained from BDH/VWR International (West Chester, Pa.).

Alumina microbeads ($Al_2O_3$ Microbeads)—refers to neutral, non-acidic alumina microbeads (100-200 mesh) commercially available under the trade designation AG7 from BioRad Laboratories (Berkeley, Calif.).

Alumina spheres ($Al_2O_3$ Spheres or "tonerde kugeln")—refers to alumina spheres having a diameter of 1.78 mm and having a surface area of 207 m²/g, and commercially available as 1.8/210 spheres from Sasol Germany GmbH.

APTS—refers to (aminopropyl)triethoxy silane obtained from Alfa Aesar; (Ward Hill, Mass.).

Aqueous KOH—refers to a 1 M potassium hydroxide solution prepared with potassium hydroxide (KOH) obtained from BDH/VWR International (West Chester, Pa.).

Basic dimethylglyoxime solution—refers to a solution prepared by mixing 0.12 g dimethylglyoxime, 11.56 g Aqueous KOH, and 28.32 g deionized water.

DEDMS—refers to diethoxydimethylsilane obtained from Alfa Aesar (Ward Hill, Mass.).

DI water—refers to deionized water.

Dimethylglyoxime was obtained from Mallinckrodt (New York, N.Y.).

HMDS—refers to hexamethyldisilazane obtained from Alfa Aesar (Ward Hill, Mass.).

Nickel acetate solution—refers to a 5 weight percent (wt %) solution of nickel acetate dissolved in dionized water. The nickel acetate tetrahydrate ($Ni(OAc)_2 \cdot 4H_2O$) was obtained from EM Science (Gibbstown, N.J.). OTS—refers to n-octadecyltrichlorosiliane obtained from Alfa Aesar (Ward Hill, Mass.).

PFODMS—refers to 1H,1H,2H,2H-perfluorooctyldimethychlorosilane obtained from Lancaster (Pelham, N.H.).

Toluene was obtained from EMD (Gibbstown, N.J.).

Silica microbeads ($SiO_2$ microbeads)—refers to 150-230 mesh silica microbeads having a surface area of 500-600 m²/g that are commercially available under the trade name SILICA GEL 60 from Alfa Aesar (Ward Hill, Mass.).

Preparatory Example P1
($Ni^{2+}$/Dimethylglyoxime/$SiO_2$ Microbeads)

Silica microbeads (3.57 g) were added to a nickel acetate solution (11.08 g) in a flask and swirled for 12 minutes to allow adsorption/impregnation of nickel onto the surface of the silica substrate. The mixture was then vacuum-filtered over a #5 Whatman filter paper in a 125 mm Buchner funnel and washed twice with DI water. The microbeads were placed in a vial and basic dimethylglyoxime solution (17.6 g) was added. The color of the microbeads rapidly changed from white to pink with a pink supernatant. The solids were washed with DI water and decanted several times to remove nickel dimethylglyoxime residues. A film of nickel dimethylglyoxime that formed on the surface of the solution was skimmed off. The washed and filtered microbeads were then transferred to a glass Petri dish and dried in an oven at 110°

C. for 1-2 hours in air. The dried $Ni^{2+}$/dimethylglyoxime/ $SiO_2$ microbeads were green-yellow in color.

Figure 1A:
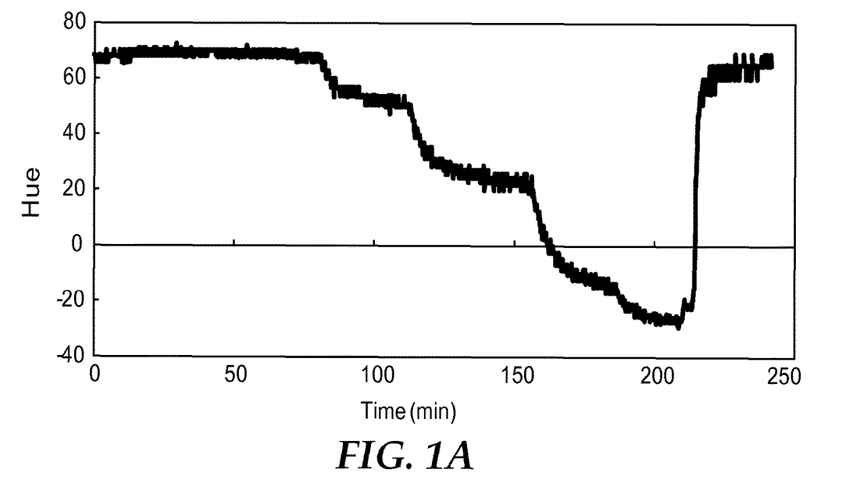
FIG. 1A is a graph of the change in Hue versus time for Preparatory Example P1.
Figure 1B:
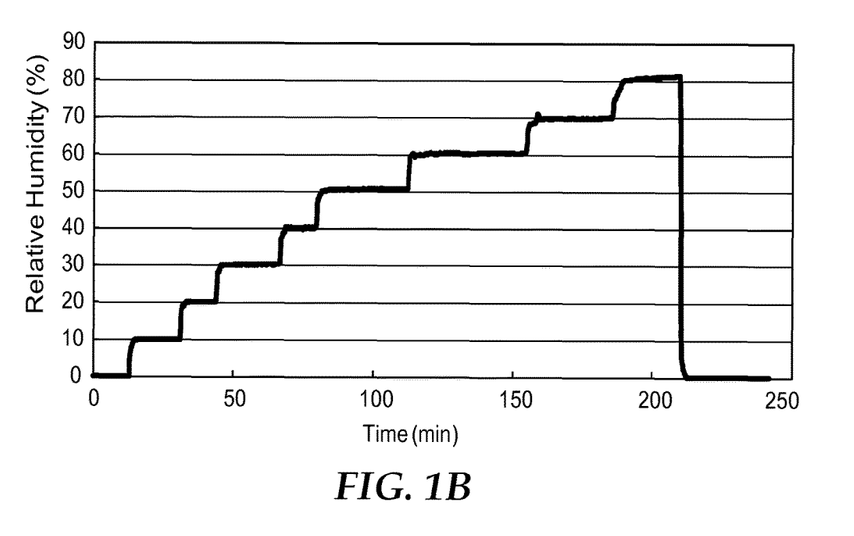
FIG. 1B is a graph of the percent relative humidity versus time for Preparatory Example P1.

A reflectance spectrum was measured according to the Optoelectronic Test Method above for the $Ni^{2+}$/dimethylglyoxime/$SiO_2$ microbeads at 10% RH increments from 0% to 90%. The microbeads were held at each relative humidity level until no further change in Hue was detected for 30 minutes. The data from the spectrum was converted to a graph of Hue vs time in minutes, as shown in FIG. 1A, and correlated to a graph of relative humidity (%) vs time, as shown in FIG. 1B.

Example 1—$Ni^{2+}$/Dimethylglyoxime/DEDMS-Modified $SiO_2$ Microbeads

DEDMS (0.53 g) was added to acetic acid solution (25.07 g) to form an emulsion having about 2.07 wt % DEDMS. The emulsion was vortex mixed and swirled for about 3 minutes and became a clear, colorless solution. Silica microbeads (2.52 g) were added and mixed by hand for 5 minutes, and then washed and decanted three times with DI water. The beads were vacuum-filtered in a Buchner funnel over a #5 Whatman filter paper, and further washed on the filter several times before drying on a glass Petri dish in an oven at 110° C. for 10 minutes.

The dried microbeads were cooled to room temperature and then immersed in a 5.08 g of nickel acetate solution for 10 minutes. The mixture increased in viscosity, but was mixable by hand. The beads were then washed and decanted three times with DI water to remove excessive solution on the surface of the beads, vacuum filtered over a #5 Whatman filter paper on a Buchner funnel, and washed several times on the filter with DI water. The wet beads were transferred to a large glass jar and 10.15 g of basic dimethylglyoxime solution were added quickly and allowed to mix for 60 seconds. The beads were then thoroughly washed and decanted several times with DI water. The wet beads were dried in a glass Petri dish for 2 hours at 110° C. in air. The resulting dried $Ni^{2+}$/dimethylglyoxime/DEDMS-modified $SiO_2$ microbeads were light yellow in color.

Example 2 ($Ni^{2+}$/Dimethylglyoxime/PFODMS-Modified $SiO_2$ Microbeads)

Silica microbeads (1.9956 g) were immersed in 4 mL of a 1% v/v solution of PFODMS in toluene and gently shaken for 5 minutes. The PFODMS-modified microbeads were then rinsed with toluene and DI water and filtered over a #1 Whatman filter paper on a Buchner funnel. The beads were dried in an oven at 110° C. for 30 minutes, and the cooled microbeads were transferred to a vial.

A nickel acetate solution (10.10 g) was added to the PFODMS modified silica microbeads (~1.39 g). Immediately after the solution was added, the beads clumped and floated to the surface of the solution and quickly turned a green color. The mixture was swirled by hand and the beads settled to the bottom of the vial. The mixture was swirled and vortex mixed several times, then left at room temperature for 10 minutes and then decanted. The microbeads were washed with DI water and decanted three times, and then vacuum filtered over a #5 Whatman filter paper in a funnel. The microbeads were washed again on the filter. The beads were carefully transferred to a vial, and 5.58 g of basic dimethylglyoxime solution was added. After the solids settled, the mixture was decanted and the solids were washed with DI water and decanted three times to remove most of the residue. After the microbeads settled to the bottom, a paper towel was inserted into the vial to remove the remaining residue floating in the water above the microbeads. The microbeads were then vacuum-filtered over a #5 Whatman filter paper in a Buchner funnel, and then washed thoroughly on the filter with DI water. Any residues on the surface of the wash water in the filter funnel were skimmed from the surface. Bright pink microbeads were transferred to a glass Petri dish and dried at 110° C. in air for 60 minutes. The resulting dried $Ni^{2+}$/dimethylglyoxime/PFODMS-modified $SiO_2$ microbeads were green-yellow in color.

Example 3 ($Ni^{2+}$/Dimethylglyoxime/OTS-Modified $SiO_2$ Microbeads)

Silica microbeads (1.9983 g) were immersed in 4 mL of a 1% v/v solution of OTS in toluene and mixed for 5 minutes before rinsing with toluene and DI water. The treated beads were filtered over a #1 Whatman filter paper in a funnel and dried at 110° C. for 30 minutes. A nickel acetate solution (5.09 g) was added to the dried the OTS-modified silica microbeads (1.51 g) in a vial and the mixture was mixed for 10 minutes at room temperature. The beads were DI water-washed and decanted three times to remove excessive solution on the surface of the beads prior to direct, rapid addition of basic dimethylglyoxime solution (5.30 g). The mixture was allowed to mix for 60 seconds before the beads were washed/decanted several times to remove residue and pink colored solution. The mixture was then vacuum-filtered over a #5 Whatman filter paper. The beads were then transferred to a glass Petri dish and dried for 60 minutes at 110° C. in air. The resulting $Ni^{2+}$/dimethylglyoxime/OTS-modified $SiO_2$ microbeads were green-yellow in color.

Comparative Example 1 and Examples 4-6 (Indicator Tapes)

Indicator tapes in Comparative Example 1 and Examples 4-6 were prepared and tested as described above using the moisture-indicating compositions from Example P1 and Examples 1-3, respectively.

Figure 2:
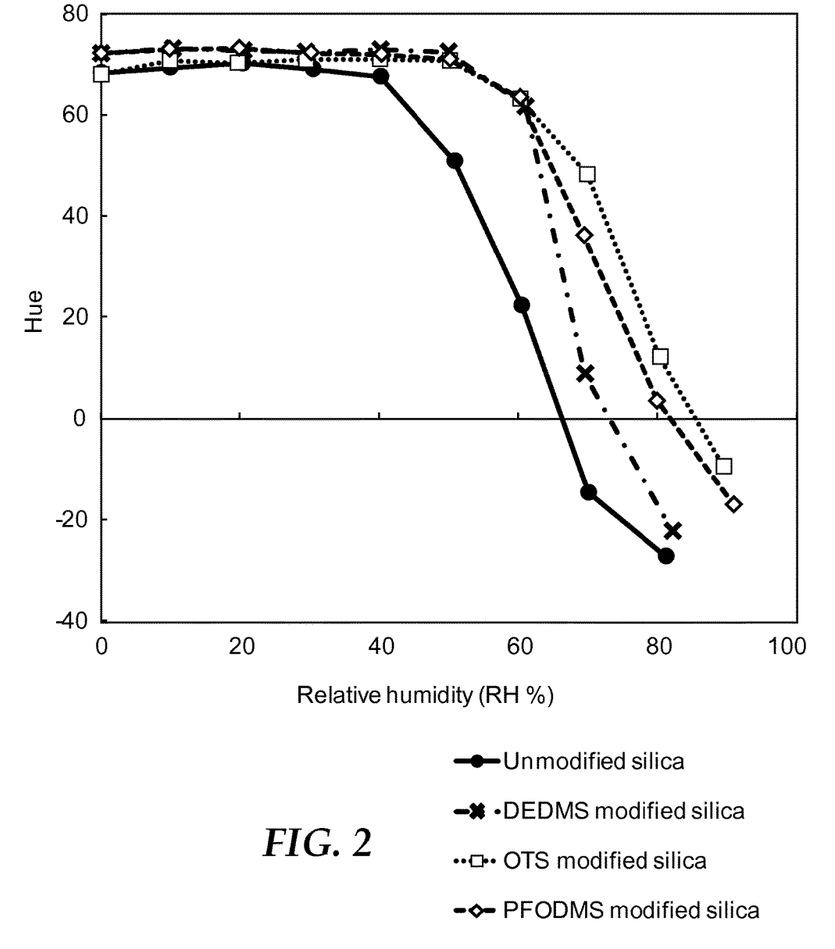
FIG. 2 is a graph of the change in Hue versus percent relative humidity for various indicator tapes (Examples 4, 5, 6, and 7) prepared with the compositions of Examples P1, 1, 2, and 3.

The reflectance spectra for the indicator tapes of Comparative Example 1 and Examples 4-6 were measured and converted to Hue as described above in the Optoelectronic Test Method. FIG. 2 shows the change in Hue of unmodified silica microbeads (Comparative Example 1) and modified silica microbeads (Examples 4-6; DEDMS-modified silica, OTS-modified silica, and PFODMS-modified silica) at various humidity levels. The humidity level showing significant color change was shifted to higher % RH levels for the modified silica microbeads as compared to the unmodified silica.

Table 1 shows the RGB expressed color from reflection spectra. The data in Table 1 show significant color changes for DEDMS-modified, PFODMS-modified, and OTS-modified silica occurred at RH levels of 60~70%, 70~80%, and 80%, respectively. Table 1 illustrates that the color change of modified silica can be shifted to a higher % RH level than from the unmodified silica microbeads of Comparative Example 1 (beads from Example P1) due to the hydrophobicity imparted by the hydrophobic silyl groups on the silica surface.

TABLE 1

| Ex | Indicator Composition | Color at Varying Relative Humidities | | | | | | | | |
|---|---|---|---|---|---|---|---|---|---|---|
|  |  | 0% | 10% | 20% | 30% | 40% | 50% | 60% | 70% | 80% |
| CE1 | Ex P1 | Green-Yellow | Green-Yellow | Green-Yellow | Green-Yellow | Green-Yellow | Yellow | Orange-Pink | Pink | Pink |
| 4 | Ex 1 | Green-Yellow | Green-Yellow | Green-Yellow | Green-Yellow | Green-Yellow | Green-Yellow | Green-Yellow | Pink | Pink |
| 5 | Ex 2 | Green-Yellow | Green-Yellow | Green-Yellow | Green-Yellow | Green-Yellow | Green-Yellow | Green-Yellow | Orange-Pink | Pink |
| 6 | Ex 3 | Green-Yellow | Green-Yellow | Green-Yellow | Green-Yellow | Green-Yellow | Green-Yellow | Green-Yellow | Yellow | Pink |

Example 7 (Ni$^{2+}$/Dimethylglyoxime/APTS-Modified SiO$_2$ Microbeads)

An acetic acid solution (24.61 g) of was added to APTS (0.75 g) in a glass vial, and a hazy solution formed immediately. The solution became less hazy after vortex mixing for 1-2 minutes. Silica microbeads (2.50 g) were added to the solution and mixed for 5 minutes by hand and by vortex mixing. The beads were then washed with 40 mL of DI water and decanted three times, and then vacuum-filtered over #5 Whatman filter paper in a Buchner funnel. The microbeads were washed with water on the filter, transferred to a glass Petri dish and allowed to dry in an oven at 110° C. in air for 10 minutes. The cooled microbeads were collected in a vial.

A nickel acetate solution (~10 g) was added to the APTS-modified silica gel (~2.83 g). The beads quickly turned green in color and settled to the bottom of the vial with swirling by hand. The mixture was swirled and vortex mixed several times and then allowed to sit at room temperature for 10 minutes. The beads were washed with DI water and decanted three times before vacuum filtering over a #5 Whatman filter paper in a funnel, followed with an additional wash with DI water on the filter. The beads were then transferred to a vial, and 10.76 g of basic dimethylglyoxime solution was added. The beads immediately changed to a red color, with simultaneous formation of red residue in the solution. The solution did not appear highly colored. The microbeads were washed with DI water and decanted three times to remove most of the residues. Any residue at the surface was removed with a paper towel that was inserted into the vial after the microbeads settled. The solids were then vacuum-filtered over a #5 Whatman filter paper in a Buchner funnel, and washed thoroughly on the filter with additional DI water. Floating/suspended residues were skimmed off of the surface of the wash during filtration. The beads were then carefully transferred to a glass Petri dish, dried at 110° C. for 60 minutes and collected in a vial. The dried Ni$^{2+}$/dimethylglyoxime/APTS-modified SiO$_2$ microbeads were yellow-green in color.

Example 8 (Ni$^{2+}$/Dimethylglyoxime/APTS-DEDMS-Modified SiO$_2$ Microbeads)

A clear solution was prepared by mixing 0.50 g of DEDMS with 0.76 g of APTS. A hazy solution formed immediately after adding 24.79 g of acetic acid. The solution became less hazy after vortex mixing for 3-4 minutes. The resulting hazy solution had no noticeable emulsion drops in it when viewed with a loupe at 4× magnification. Silica microbeads (2.50 g) were added to the solution and mixed for 5 minutes by hand and vortex mixing. The microbeads were then washed and decanted three times with 40 mL of DI water, and then vacuum filtered over a #5 Whatman filter paper on a Buchner funnel, followed by an additional wash with DI water on the filter. The beads were then transferred to a glass Petri dish and dried in an oven at 110° C. in air for 10 minutes. Cooled beads were collected in a vial.

Approximately 10 g of nickel acetate solution were added to the DEDMS-APTS-modified silica microbeads (~2.93 g). The beads initially clumped and floated to the surface of the solution. After vortex mixing the clumps broke apart and the beads remained separated and settled to the bottom of the vial. The mixture was swirled and vortex mixed several times and then allowed to settle at room temperature for 10 minutes. The beads were then washed with DI water and decanted three times, and then vacuum filtered over a #5 Whatman filter paper in a Buchner funnel) followed with an additional wash with DI water on the filter. The microbeads were carefully transferred to a vial, and 10.76 g of basic dimethylglyoxime solution was added. The microbeads immediately changed to a red color, and red solid residues formed simultaneously in the solution. The solution did not appear highly colored. The beads were washed with DI water and decanted three times to remove most of the residuals. Remaining residues in the solution were removed with a paper town inserted into the water over the microbeads. The washed microbeads were then transferred to a glass Petri dish, dried at 110° C. for 60 minutes and collected in a vial when cooled. The dried Ni$^{2+}$/dimethylglyoxime/APTS-DEDMS-modified SiO$_2$ microbeads were yellow-green in color.

Examples 9-10 (Indicator Tapes)

Figure 3:
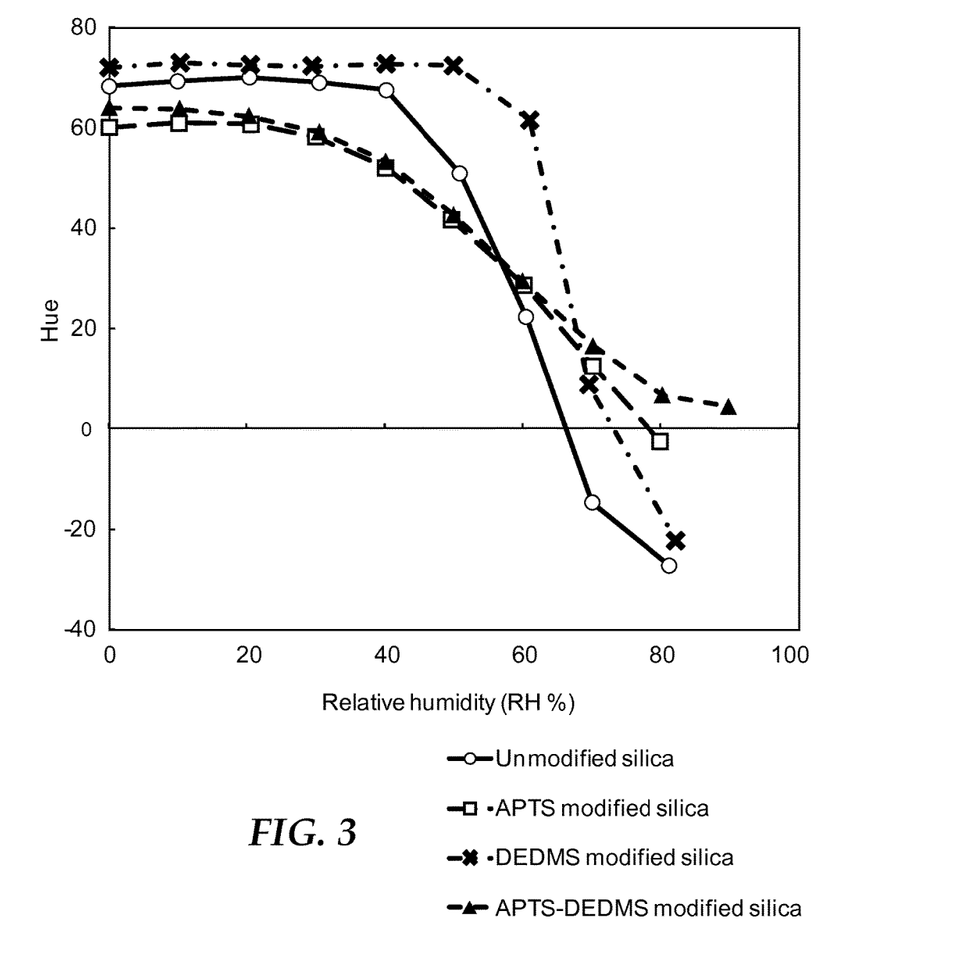
FIG. 3 is a graph of the change in Hue versus percent relative humidity for various indicator tapes (Examples 4, 5, 10, and 11) prepared with the compositions of Examples P1, 1, 8, and 9.

Indicator tapes were prepared as described above using the moisture indicating compositions of Examples 7 and 8 for Examples 9 and 10, respectively. The reflectance spectra for the indicator tapes of Comparative Example 1 and Examples 4, 9, and 10 were measured and converted to Hue as described above. FIG. 3 shows the change in Hue values with changing RH for Comparative Example 1 and Examples 4, 9, and 10. The RH values over which a significant change in Hue value occurred corresponded to the range over which a significant color change occurred for the moisture-indicating composition. The RH, at which significant color change occurred for the APTS-modified moisture-indicating composition (Example 9), shifted to an RH value below that of the unmodified moisture-indicating composition (Comparative Example 1). The indicator tape prepared from a combination of hydrophilic and hydrophobic silane (APTS and DEDMS, respectively,) modified moisture-indicating composition (Example 10) showed less change at high humidity levels than the DEDMS-modified moisture-indicating composition (Example 4).

Preparatory Example P2 ($Ni^{2+}$/Dimethylglyoxime/ $Al_2O_3$ Beads)

Alumina spheres (20.08 g) were added to a nickel acetate solution (40.02 g) in a glass jar. The jar was rolled for 12 minutes at room temperature. The mixture was decanted and then vacuum filtered over a #5 Whatman filter paper in a 125 mm Buchner funnel. The beads were washed twice by adding 100 mL of DI water to the beads on the paper. The beads were then transferred to, and dried in a large glass Petri dish in an oven at 110° C. for 15 minutes.

Within 20 seconds of removing from the oven, the hot spheres were added directly into a basic dimethylglyoxime solution (40.00 g). After 2 minutes of mixing by hand, the mixture was decanted onto a #5 Whatman filter paper in a 125 mm Buchner funnel. The remainder of the mixture was vacuum filtered over the filter paper. An additional 100 mL of DI water was added twice to wash the beads on the paper. Any residues on the surface of the wash water were skimmed off with a tissue. The dark pink, uniformly colored beads were then transferred to a glass Petri dish and dried for 90 minutes at 110° C. in air (mixed once after 60 minutes of drying). The dried $Ni^{2+}$/dimethylglyoxime/$Al_2O_3$ beads (18.90 g) were yellow to dark yellow in color.

Example 11 ($Ni^{2+}$/Dimethylglyoxime/HDMS-Modified $Al_2O_3$ Beads)

Alumina beads (3.11 g) were dried in an oven at 110° C. for 1 hour in air. The beads were placed in a small polytetrafluoroethylene (PTFE) liner cup, and a smaller alumina cup was placed on top of the spheres in the liner cup. HMDS (0.38 g) was added to the smaller cup and a PTFE lid was secured on the liner cup. The PTFE assembly was carefully placed into a stainless steel autoclave reactor (Model 4749 General Purpose Acid Digestion Vessel, 23 mL capacity, Parr Instruments) that was secured and placed in an oven held at 110° C. for 16 hours. The reactor was then left to cool to room temperature in a fume hood for several hours before opening. The beads were transferred to a glass Petri dish and heated at 110° C. in air for 5 minutes.

The HDMS modified beads (3.26 g) were immersed in 8.16 g of nickel acetate solution for about 14 minutes. The beads were then thoroughly washed with DI water wash/decant cycles to remove most of the residual nickel solution. A basic dimethylglyoxime solution (5.10 g) was added to the wet beads, and the mixture was allowed to mix for 60 seconds before thoroughly washing the beads with DI water and decanting several times to remove pink/red residues from the surface of the beads and solution. The washed beads were then dried at 110° C. in air for 2.5 hours. The $Ni^{2+}$/dimethylglyoxime/HDMS-modified $Al_2O_3$ beads were green-yellow in color.

Figure 4:
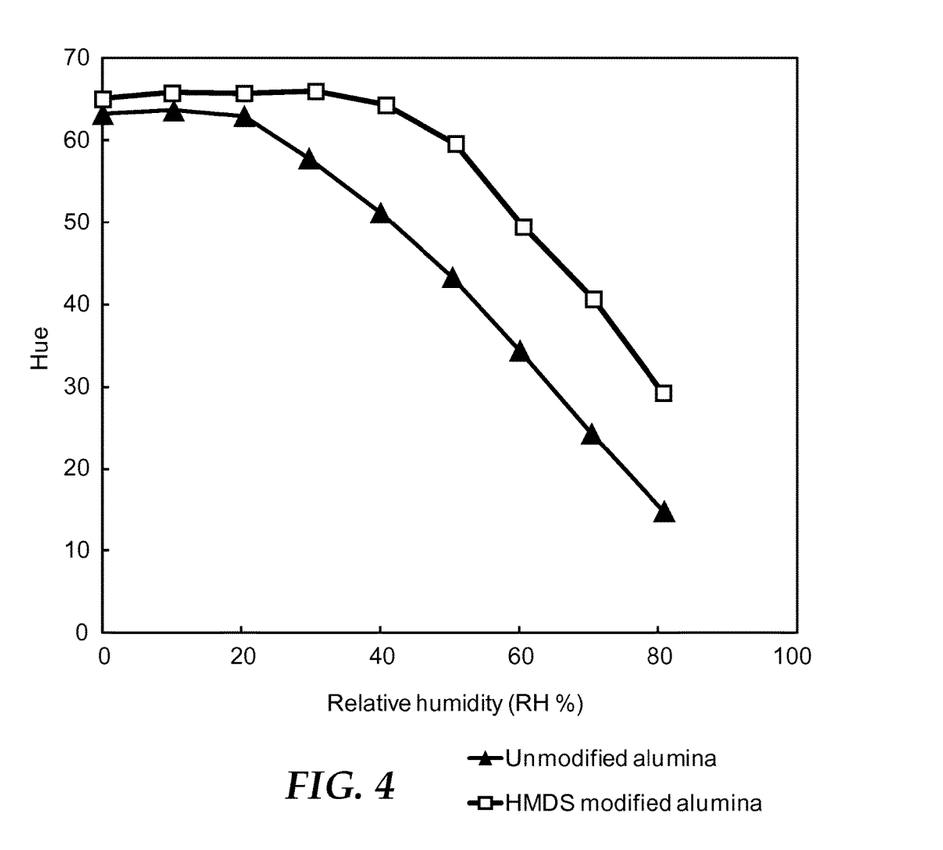
FIG. 4 is a graph of the change in Hue versus percent relative humidity for an indicator card (Example 13) having various indicator tapes prepared with the compositions of Examples P1, 1, 3, and 8.

Reflection spectra were measured and converted to Hue the moisture indicating compositions of Example P2 and Example 11 according to Testing of Moisture Indicating Compositions described above. FIG. 4 shows significant Hue change for unmodified alumina moisture indicating beads (Example P2) occurred at 50-60% RH. $Ni^{2+}$/dimethylglyoxime/HMDS-modified $Al_2O_3$ beads showed a significant change in Hue value between 70 and 80% RH.

Example 13 (Moisture Indicating Card)

A moisture indicating card was prepared with moisture indicating compositions selected to show a color change when exposed to humidity levels to be monitored. To illustrate the concept, indicator tapes were prepared as described above using the moisture-indicating compositions as follows: Tape I—$Ni^{2+}$/dimethylglyoxime/APTS-modified $SiO_2$ microbeads (Example 7); Tape II—$Ni^{2+}$/dimethylglyoxime/$SiO_2$ microbeads (Example P1); Tape III—$Ni^{2+}$/dimethylglyoxime/DEDMS-modified $SiO_2$ microbeads (Example 1); and Tape IV—$Ni^{2+}$/dimethylglyoxime/OTS-modified $SiO_2$ microbeads (Example 3). The indicator tapes were placed adjacent to each other to form an array, in order from Tape I to Tape IV, in the test chamber so that the tapes were simultaneously exposed to the same % RH level from 0% to 90% in 10% increments. The indicator tapes were first exposed to 0% RH for 30 minutes. A digital image was taken using a digital camera (Canon PowerShot SD960 IS, macro-mode) as no color change occurred, and the % RH was increased to the next level. If no change in color occurred in any of the indicator tapes for 30 minutes, a digital image was taken and the % RH was increased. If a color change occurred, the indicator tapes were held at that % RH level until no further change was observed for 30 minutes. The duration of exposure ranged from 30 minutes to 60 minutes. Digital images that were taken at each % RH level were merged to produce an image of the arrays to show color changes at various % RH. The array colorimetrically indicated exposure to humidities of 50%, 60%, 70%, and 80% RH for Tapes I—IV, respectively, as shown in Table 2.

TABLE 2

| | Color at varying relative humidity levels | | | | | | | | | |
|---|---|---|---|---|---|---|---|---|---|---|
| Tape | 0% | 10% | 20% | 30% | 40% | 50% | 60% | 70% | 80% | 90% |
| I | Yellow-Green | Yellow-Green | Yellow-Green | Yellow-Green | Yellow | Yellow | Orange-Pink | Orange-Pink | Pink | Pink |
| II | Green-Yellow | Green-Yellow | Green-Yellow | Green-Yellow | Green-Yellow | Yellow | Orange-Pink | Pink | Pink | Pink |
| III | Green-Yellow | Green-Yellow | Green-Yellow | Green-Yellow | Green-Yellow | Green-Yellow | Yellow | Pink | Pink | Pink |
| IV | Green-Yellow | Green-Yellow | Green-Yellow | Green-Yellow | Green-Yellow | Green-Yellow | Green-Yellow | Yellow | Pink | Pink |

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows. All references cited in this disclosure are herein incorporated by reference in their entirety.

What is claimed is:

1. A composition comprising:
   a solid metal oxide support having surface hydroxyl groups;
   a silyl-containing compound bound to the solid metal oxide support through a silanol bond with the surface hydroxyl groups; and
   a bis(glyoxime)-transition metal complex bound to the solid metal oxide support;
   wherein the composition is a reversible colorimetric moisture-indicating composition.

2. The composition of claim 1, wherein the silyl-containing compound is of Formula (I)

$$R^1\text{—Si}(R^2)_{3-x}(R^3)_x \qquad (I)$$

wherein
   $R^1$ is an alkyl, fluoroalkyl, alkyl substituted with an amino, aryl, aralkyl, or alkaryl group;
   each $R^2$ is independently hydroxyl or a hydrolyzable group;
   each $R^3$ is independently a non-hydrolyzable group; and
   x is an integer equal to 0, 1, or 2.

3. The composition of claim 1, wherein the silyl-containing compound is of Formula (II)

$$(R^3)_x(R^2)_{3-x}\text{Si—}R^4\text{—Si}(R^2)_{3-x}(R^3)_x \qquad (II)$$

wherein
   $R^4$ is an alkylene, arylene, or a combination thereof;
   each $R^2$ is independently hydroxyl or a hydrolyzable group;
   each $R^3$ is independently a non-hydrolyzable group; and
   x is an integer equal to 0, 1, or 2.

4. The composition of claim 1, wherein the silyl-containing compound is selected from the group consisting of diethoxydimethylsilane, hexamethyldisilazane, n-octadecyltrichlorosilane, 1H,1H,2H,2H-perfluoroctyldimethylchlorosilane, and (3-aminopropyl)triethoxysilane.

5. The composition of claim 1, wherein no more than about 50% of surface hydroxyl groups of the support are bound to the silyl-containing compound.

6. The composition of claim 1, wherein the solid metal oxide support comprises an oxide of aluminum, silicon, or a combination thereof.

7. The composition of claim 1, wherein the transition metal in the bis(glyoxime)-transition metal complex comprises rhodium, iridium, platinum, palladium, gold, nickel, copper, or a combination thereof.

8. The composition of claim 1, wherein the bis(glyoxime)-transition metal complex comprises bis(dimethylglyoximato)-nickel(II).

9. The composition of claim 1, wherein the composition quantitatively changes optical spectrum at relative humidities ranging from about 50% to about 90% relative humidity at 25° C.

10. A colorimetric relative humidity-indicating sensor comprising:
    a reversible colorimetric moisture-indicating composition comprising
       a solid metal oxide support having surface hydroxyl groups;
       a silyl-containing compound bound to the solid metal oxide support through a silanol bond with the surface hydroxyl groups; and
       a bis(glyoxime)-transition metal complex bound to the solid metal oxide support; and
    wherein the optical spectrum of the sensor changes quantitatively according to the relative humidity within the environment within which the sensor is placed.

11. The sensor of claim 10, wherein the silyl-containing compound is of Formula (I)

$$R^1\text{—Si}(R^2)_{3-x}(R^3)_x \qquad (I)$$

wherein
   $R^1$ is an alkyl, fluoroalkyl, alkyl substituted with an amino, aryl, aralkyl, or alkaryl group;
   each $R^2$ is independently hydroxyl or a hydrolyzable group;
   each $R^3$ is independently a non-hydrolyzable group; and
   x is an integer equal to 0, 1, or 2.

12. The sensor of claim 10, wherein the silyl-containing compound is of Formula (II)

$$(R^3)_x(R^2)_{3-x}\text{Si—}R^4\text{—Si}(R^2)_{3-x}(R^3)_x \qquad (II)$$

wherein
   $R^4$ is an alkylene, arylene, or a combination thereof;
   each $R^2$ is independently hydroxyl or a hydrolyzable group;
   each $R^3$ is independently a non-hydrolyzable group; and
   x is an integer equal to 0, 1, or 2.

13. The sensor of claim 10, wherein no more than about 50% of surface hydroxyl groups of the support are bound to the silyl-containing compound.

14. The sensor of claim 10, wherein the solid metal oxide support comprises an oxide of aluminum, silicon, or a combination thereof.

15. The sensor of claim 10, wherein the bis(glyoxime)-transition metal complex comprises bis(dimethylglyoximato)-nickel (II).

16. The sensor of claim 10, wherein the sensor quantitatively changes optical spectrum at relative humidities ranging from about 50% to about 90% relative humidity at 25° C.

17. The sensor of claim 10, wherein the sensor quantitatively changes optical spectrum at relative humidities ranging from about 60% to about 80% relative humidity at 25° C.

18. A method of adjusting the colorimetric response of a moisture-indicating composition comprising:
    modifying the surface of a solid metal oxide support having surface hydroxyl groups by reacting the surface hydroxyl groups of the solid metal oxide support with a silyl-containing compound to create a modified solid metal oxide support; and
    bonding a bis(glyoxime)-transition metal complex to the modified solid metal oxide support to create a reversible colorimetric moisture-indicating composition.

19. The method of claim 18, wherein the silyl-containing compound is of Formula (I)

$$R^1\text{—Si}(R^2)_{3-x}(R^3)_x \qquad (I)$$

wherein
   $R^1$ is an alkyl, fluoroalkyl, alkyl substituted with an amino, aryl, aralkyl, or alkaryl group;
   each $R^2$ is independently hydroxyl or a hydrolyzable group;
   each $R^3$ is independently a non-hydrolyzable group; and
   x is an integer equal to 0, 1, or 2.

20. The method of claim 18, wherein the silyl-containing compound is of Formula (II)

(II)

wherein
- $R^4$ is an alkylene, arylene, or a combination thereof;
- each $R^2$ is independently hydroxyl or a hydrolyzable group;
- each $R^3$ is independently a non-hydrolyzable group; and
- x is an integer equal to 0, 1, or 2.

21. The method of claim 18, wherein no more than about 50% of surface hydroxyl groups of the support are bound to the silyl-containing compound.

22. The method of claim 18, wherein the solid metal oxide support comprises an oxide of aluminum, silicon, or a combination thereof.

23. The method of claim 18, wherein the bis(glyoxime)-transition metal complex comprises bis(dimethylglyoximato)-nickel (II).

24. The method of claim 18, wherein the moisture-indicating composition quantitatively changes optical spectrum at relative humidities ranging from about 50% to about 90% relative humidity at 25° C.

25. The method of claim 18, wherein the moisture-indicating composition quantitatively changes optical spectrum at relative humidities ranging from about 60% to about 80% relative humidity at 25° C.

* * * * *